United States Patent
Marzilli et al.

(10) Patent No.: US 6,599,283 B1
(45) Date of Patent: Jul. 29, 2003

(54) METHOD OF PREVENTING REPERFUSION INJURY

(75) Inventors: Mario Marzilli, Livorno (IT); Brent Blackburn, Los Altos, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/848,809

(22) Filed: May 4, 2001

(51) Int. Cl.⁷ .............................................. A61M 31/00
(52) U.S. Cl. ....................................................... 604/509
(58) Field of Search ........................ 604/96.01, 103.01, 604/103.02, 509, 508, 915, 101.01–101.05

(56) References Cited

U.S. PATENT DOCUMENTS

| | | | | |
|---|---|---|---|---|
| 5,206,222 A | * | 4/1993 | Forman et al. ................ 514/46 |
| 5,504,090 A | * | 4/1996 | Neely ........................ 514/263 |
| 5,573,772 A | * | 11/1996 | Downey et al. ............ 424/423 |
| 5,609,574 A | * | 3/1997 | Kaplan et al. ................ 604/53 |
| 5,662,609 A | * | 9/1997 | Slepian ........................ 604/101 |
| 5,733,916 A | * | 3/1998 | Neely ........................ 514/262 |
| 6,001,842 A | * | 12/1999 | Neely ........................ 514/263 |
| 6,339,072 B2 | * | 1/2002 | Martin et al. ................. 514/46 |

OTHER PUBLICATIONS

Marzilli, M., Orsini, E., Marraccini, P., Testa, R.; Beneficial effects of intracoronary adenosine in acute myocardial infarction. Circulation. May 2000;101:2154–2159.

Vander Heide, R., Reimer, K.; Effect of adenosine therapy at reperfusion on myocardial infarct size in dogs. Cardiovascular Research 1996;31:711–718.

Babbitt, D., Virmani, R., Forman M.; Intracoronary adenosine administered after reperfusion limits vascular injury after prolonged ischemia in the canine model. Circulation. 1989;80:1388–1399.

* cited by examiner

Primary Examiner—Manuel Mendez
(74) Attorney, Agent, or Firm—CV Therapeutics, Inc.

(57) ABSTRACT

Methods are disclosed for preventing or inhibiting reperfusion injury to the ischemic myocardium.

10 Claims, No Drawings

METHOD OF PREVENTING REPERFUSION INJURY

BACKGROUND

1. Field of the Invention

This invention relates to a method of preventing or inhibiting reperfusion injury to the ischemic myocardium, comprising administration of adenosine or an adenosine receptor agonist via a catheter prior to reperfusion of the myocardium.

2. Introduction

Coronary arteries are subject to atherosclerosis. During this process, plaque forms within vascular regions, resulting in stenosed regions having reduced cross-sectional area. The reduced area causes a reduction in transport of blood, oxygen, and nutrients through the arteries, which can result in ischemia, necrosis, angina, myocardial infarction, and ultimately death.

A commonly used method for treating atherosclerosis is percutaneous transluminal coronary angioplasty (PTCA). PTCA includes insertion of a balloon catheter into the blocked coronary artery, and continuing until the uninflated balloon portion is placed across the stenosed region. The balloon is inflated, physically widening the narrowed vessel. The balloon is then deflated, thus causing reperfusion of the artery.

Unfortunately, reperfusion, although it relieves or reduces the problems caused by ischemia, is often followed by morphological and functional changes that ultimately result in tissue damage known as reperfusion injury, which significantly reduces the benefit of reperfusion. Reperfusion injury can be caused by either an acceleration of processes initiated during ischemia per se, or new pathophysiological changes that are initiated by the reperfusion itself. As a result, myocardium that was viable at the end of the ischemic period may nonetheless lose viability during reperfusion.

Although the precise mechanism of reperfusion injury is uncertain, there is support for neutrophil-mediated cell injury as a contributing factor. Other possible mechanisms include platelet aggregation, vascular injury, local release of vasoactive substances, and depletion of the myocardial nucleotide pool.

Adenosine, an endogenous purine nucleoside, antagonizes many of the biochemical and physiological mechanisms implicated in reperfusion injury. However, adenosine is unsuitable for conventional administration, for example orally. Adenosine has a short half life in blood plasma, and is thus also unsuitable for IV administration.

It is known that adenosine attenuates ischemia-reperfusion injury of the heart upon administration prior to ischemia. Ely, S W et al., J. Thorac Cardiovasc Surg 90:549–556, 1985; Olafsson B, et al. Circ 76:1135–1145, 1987; Lasley, R D, et al., Am J Physiol 263:H1460–H1465, 1992; Ely S W, Berne R M, Circ 85:893–904, 1992; Janier, M F, et al., Am J Physiol 264:H163–H170, 1993; Zhao, Z Q, et al. Circ 88:709–719, 1993. It has been postulated that adenosine provides a protective effect by acting on $A_1$ adenosine receptors or on $A_2$ adenosine receptors.

Thus, it would be useful to provide a method for delivering adenosine, or compounds that are $A_1$ and/or $A_2$ adenosine receptor agonists, to a reperfused site in a manner that prevents reperfusion injury, in particular to a reperfused site following angioplasty.

SUMMARY OF THE INVENTION

In one aspect, the invention provides a method of preventing or inhibiting ischemia-reperfusion injury to a human following angioplasty, comprising:

a) positioning a balloon catheter proximate to the obstruction of the infarct-related artery and inflating the balloon;
b) contacting the distal vascular bed with an adenosine receptor agonist; and
c) deflating the balloon.

Optionally, the dilated coronary segment can be stented following treatment.

The adenosine receptor agonist is preferably chosen from adenosine, or an $A_1$ and/or $A_2$ adenosine receptor agonist. Preferred $A_1$ or $A_2$ adenosine receptor agonists are adenosine, N-[(3R)-tetrahydro-3-furanyl] (CVT 510) and 1-{9-[(4S,2R,3R,5R)-3,4-dihydroxy-5-(hydroxymethyl)oxalan-2-yl)]-6-aminopurine-2-yl}pyrazol-4-yl)-N-methylcarboxamide (CVT-3146). Most preferably, the compound chosen for administration is adenosine, which is introduced into the distal bed via injection.

DETAILED DESCRIPTION OF THE INVENTION

Early reperfusion of the ischemic myocardium is known to be effective in reducing mortality from acute myocardial infarction (AMI), as is percutaneous transluminal coronary angioplasty (PCTA). Unfortunately, reperfusion, although it relieves or reduces the problems caused by ischemia, is often followed by morphological and functional changes that ultimately result in tissue damage known as reperfusion injury, which significantly reduces the benefit of reperfusion. The present invention relates to a method of preventing or inhibiting reperfusion injury following angioplasty.

It was previously known that adenosine attenuates ischemia-reperfusion injury of the heart upon administration prior to ischemia. What was not recognized was that administration of adenosine or an $A_1$ or $A_2$ adenosine receptor agonist to the distal vascular bed after insertion of the balloon catheter but prior to deflation would provide protection against reperfusion injury. The preferred agent for administration is adenosine.

In particular, the balloon catheter is advanced within the selected coronary artery, normally by means of a previously inserted guidewire, continuing until the balloon portion is placed across the stenosed region, making sure that the catheter tip is downstream of the obstruction. The balloon is then inflated, widening the narrowed vessel region. The test compound, preferably adenosine, is injected into the distal vascular bed, preferably over a period of about 30 seconds to about 2 minutes, more preferably about one minute. Injection is normally through the guidewire. The balloon is then deflated to initiate reperfusion of the ischemic area.

As used in the present specification, the following words and phrases are generally intended to have the meanings as set forth below, except to the extent that the context in which they are used indicates otherwise.

The term "percurtaneous transluminal angioplasty" refers to dilatation of a blood vessel by means of a balloon catheter, which is inserted into the chosen vessel and passed through the lumen of the vessel to the site of the lesion, where the balloon is inflated to flatten plaque against the artery wall. The balloon is then deflated and withdrawn.

The term "TIMI" flow (Thrombolysis in Myocardial Infarction) refers to an arbitrary grading system (from 1 to 3) which reflects the degree of patency in the infarct-related artery.

The term "patency" means the condition of being wide open.

The term "no-reflow phenomenon" means a condition following reperfusion in which excessive or abnormal vasoconstriction occurs.

The term "distal vascular bed" refers to the ischemic vascular tissue located at a point in the vessel beyond the region of the obstruction.

By ichemia-reperfusion injury is meant pathological changes to an organ following treatment of ischemia by reperfusion. Ischemia may be due to vascular disorders that result in occlusion of a vessel, environmental changes that occur during the harvest of a donor organ and surgical transplant to a recipient, or surgery, such as open heart surgery.

$A_1$ agonists are ligands that stimulate the $A_1$ adenosine receptor. Examples are CPA (N-cyclopentyladenosine), R-PIA (phenylisopropyladenosine), SDZ WAG 994 (9-[(4S,2R,3R,5R)-3-hydroxy-4-methoxy-5-(hydroxymethyl) oxalan-2-yl)-6-cyclohexylaminopurine, AMP-579 Cyclopentanecarboxamide, 4-[4-[[(1R)-1-[(3-chloro-2-thienyl)methyl]-propyl]amino]-7H-pyrrolo[2,3-d] pyrimidin-7-yl]-N-ethyl-2,3-dihydroxy-, (1S,2R,3S,4R)-N (6)-cyclopentyladenosine, CVT-510 (Adenosine, N-[(3R)-tetrahydro-3-furanyl]), and the like.

$A_{2A}$ agonists are ligands that stimulate the $A_{2A}$ adenosine receptor. Examples are WRC-0470 (2-cyclohexylmethylidenehydrazinoadenosine), CGS-21680C ((Benzenepropanoic acid, 4-[2-[[6-amino-9-(N-ethyl-.beta.-D-ribofuranuronamidosyl)-9H-purin-2-yl] amino]ethyl]monohydrochloride), AMP-579 (Cyclopentanecarboxamide, 4-[4-[[(1R)-1-[(3-chloro-2-thienyl)methyl]propyl]amino]-7H-pyrrolo[2,3-d]pyrimidin-7-yl]-N-ethyl-2,3-dihydroxy-(1S,2R,3S,4R)-2-hexynyl-neca, UK 14304 (6-Quinoxalinamine, 5-bromo-N-(4,5-dihydro-1H-imidazol-2-yl)-, [R-(R*,R*)]-2,3-dihydroxybutanedioate (1:1), MRE-0470 (Adenosine, 2-[(cyclohexylmethylene)hydrazino]), CVT-3146 (1-{9-[(4S,2R,3R,5R)-3,4-dihydroxy-5-(hydroxymethyl)oxalan-2-yl)]-6-aminopurine-2-yl}pyrazol-4-yl)-N-methylcarboxamide), and the like.

Methods and Results

Fifty four AMI patients undergoing primary PTCA were randomized to intracoronary adenosine or saline. The 2 groups were similar for age, sex, and infarct location. Patients referred for PTCA within 3 hours from the onset of AMI were considered for the study. Patients underwent diagnostic coronary angiography. If the culprit lesion was suitable for PTCA and presented with a TIMI flow from 0 to 2, the patient was included in the study and randomized after informed consent had been obtained. Patients presenting with TIMI 3 flow were diagnosed as having spontaneous reperfusion and were not included in the study.

Patients who had a history of bronchospasm and/or were undergoing therapy with theophylline derivatives and patients who had received thrombolytics in the emergency room were also excluded from the study.

Invasive Procedure

After left and right coronary arteriography by the femoral approach, a temporary pacing wire was advanced into the right ventricle and connected with a pacemaker left on demand at 60 bpm. The obstruction of the infarct-related artery was crossed with a 0.014-in guidewire, and an over-the-wire balloon catheter was positioned at the level of the obstruction. The wire was pulled out, and diluted contrast was injected through the central lumen of the catheter to confirm positioning of the catheter tip downstream of the obstruction and to assess patency of the distal vessel. The balloon was inflated, and either adenosine (4 mg in 2 mL saline) or saline (2 mL) was hand-injected into the distal vascular bed in a random fashion. The rate of injection was such as to complete treatment in 1 minute. The guidewire was then readvanced into the distal vessel, and the balloon was deflated to initiate reperfusion of the ischemic territory. The dilatation procedure was completed according to standard technique. Stenting of the dilated coronary segment was performed only for suboptimal balloon results or flow-limiting dissections. After completion of the dilation procedure, patients were observed in the catheterization room for 30 minutes. The final angiogram was then obtained, and the patient was transferred to the intensive coronary care unit. If symptoms and/or ECG changes consistent with vessel reclosure occurred during this interval, coronary angiography was performed immediately, and therapeutic measures were applied. The dilation procedure was limited to the culprit lesion in all patients.

Similarly results are obtained replacing adenosine with an $A_1$ and/or $A_2$ adenosine receptor agonist, Angiographic Analysis The angiograms were reread as a single group, in chronological sequence, by observers who had not participated in the invasive procedure and were blinded to the treatment received. Cine films were reviewed with an angiographic projection system (CAP/35 B II) allowing frame-by-frame analysis, selection, and magnification of the segments of interest. The region of interest was manually selected and digitized by a high-quality Vidicon camera. Diameter stenosis was measured by an automatic edge-detection system (Mipron, Kontron).

PTCA was considered successful when the residual stenosis was <50%, in the absence of dissection, thrombosis, or distal vessel embolization. Coronary flow was graded according to the TIMI study criteria. No-reflow was diagnosed when a reduction of $\leq 1$ TIMI grades was observed in the final angiogram relative to the post-PTCA angiogram.

Left Ventricular Function

Left ventricular function was evaluated by 2D echocardiography within 24 hours from admission and after 1 week. Echocardiography was performed with the patient lying supine with a 2.5-MHz transducer fitted to a dedicated system (Hewlett-Packard Sonos 1500). Images were recorded on S-VHS tapes and analyzed offline by 2 experienced observers blinded to the angiographic data. Four views were used: the parasternal long- and short-axis (at the level of the papillary muscle) and apical 2- and 4-chamber views. The left ventricle was divided into 16 segments. In each segment, wall motion was graded as normal, hypokinetic, akinetic, or dyskinetic. Segmental motion at admission was compared with segmental motion at 1 week to detect changes of regional function.

Metabolic Data

Creatine kinase (CK) and CK-MB were assessed every 8 hours in the first day of admission and then every day up to discharge, unless clinical events suggested repeat measurements.

Study End Points

The primary end points of this study were feasibility and safety of intracoronary adenosine administration in the setting of primary PTCA and its effect on coronary blood flow. As secondary end points, indexes of myocardial damage, including left ventricular regional function, Q-wave MI, recurrence of angina, nonfatal MI, heart failure, and cardiac death were evaluated.

Physicians in charge of the patients in the intensive coronary care unit were informed of the angiographic results of the PTCA but were blinded to the intracoronary treatment administered during the procedure.

TABLE 1

Clinical and Angiographic Characteristics

|  | Adenosine (n = 27) | Saline (n = 27) | P |
|---|---|---|---|
| Age, y | 58.5 ± 11 | 61.9 ± 9 | NS |
| Male | 22(81) | 21(78) | NS |
| Previous MI | 3(11) | 4(15) | NS |
| Time from pain onset to PTCA, min | 106 ± 81 | 126 ± 69 | NS |
| Systolic blood pressure at Admission, mm Hg | 116 ± 28 | 109 ± 22 | NS |
| Heart rate at admission, bpm | 85 ± 22 | 83 ± 17 | NS |
| Site of Infarction |  |  |  |
| Anterior | 14(52) | 16(59) |  |
| Inferior | 8(30) | 8(30) | NS |
| Inferolateral | 5(18) | 3(11) |  |
| Infarct-related artery |  |  |  |
| LAD | 13(48) | 15(56) |  |
| RCA | 9(33) | 7(26) |  |
| LCx | 2(7) | 3(11) | NS |
| Marginal | 1(4) | 2(7) |  |
| Diagonal | 2(7) | 0(0) |  |
| Multivessel disease | 16(59) | 16(59) | NS |

LAD indicates left anterior descending; LCx, left circumflex; and RCA, right coronary artery. Data are presented as mean value ± SD or number (%) of patients Statistical Analysis Data are expressed as mean±SD. Continuous variables were analyzed according to Student's t test. Dichotomous variables were compared by $X^2$ test. A value of $P<0.05$ was considered significant.

Results

Fifty-four patients were included in the study. Twenty-seven patients were randomized to adenosine and 27 to saline. The angioplasty procedure was successfully completed in all study patients. Coronary stems were implanted in 4 patients in the adenosine group and in 5 patients in the saline group (P=NS).

Demographic and clinical characteristics are presented in Table 1. The 2 groups were similar for age, sex distribution, and prevalence of previous MI. The mean times from symptom onset to first balloon inflation were similar in the 2 groups. Systolic blood pressure and heart rate at arrival in the catheterization laboratory were similar in the 2 groups. Approximately 50% of the patients presented with an anterior infarction associated with an occluded left anterior descending coronary artery and 33% with an occluded right coronary artery and inferior infarction. The remaining patients had an inferolateral infarction associated with an occluded left circumflex or marginal coronary branch. Two patients in the adenosine group had a lateral infarction associated with the occlusion of a large diagonal branch. The majority of the patients had multivessel disease.

Feasibility and Safety of Intracoronary Adenosine Administration

The intracoronary treatment procedure, including balloon inflation, removal of the guidewire, administration of the treatment drug, readvancement of the wire into the distal vessel, and deflation of the balloon, was completed in <2 minutes in all patients. The injections of adenosine or saline in the distal coronary bed were well tolerated and free of side effects. No patients complained of worsening of chest pain, and no patients suffered from hemodynamic instability. No bradyarrhythmias or tachyarrhythmias were associated with this protocol, including adenosine injection into the right coronary artery.

Angiographic Results

Angiographic success, defined as a residual stenosis <50% in the absence of dissection (grade ≧3 by American Heart Association/American College of Cardiology classification), thrombosis, or distal embolization was achieved in all patients. Residual diameter stenosis by quantitative coronary arteriography was 27.8±9.5% in the adenosine group and 34.41–8.7% in the saline group (P=NS). At the end of the dilation procedure, flow in the infarct-related artery was graded TIMI 3 in all adenosine patients. In the saline group, 19 patients achieved a TIMI 3 flow and 8 patients a TIMI 2 flow (P<0.05).

The no-reflow phenomenon, defined as a drop of ≧1 TIMI grades of coronary flow in the final angiogram relative to the post-PTCA angiogram, was diagnosed in 1 patient in the adenosine group and in 7 patients in the saline group (P<0.02). Of these 7 patients, 4 had achieved a TIMI 3 flow and 3 a TIMI 2 flow after PTCA. In 6 patients, no-reflow manifested with recurrence or worsening of chest pain and/or ST-segment changes and occurred from 5 to 12 minutes after the last balloon inflation. Treatment of no-reflow included intracoronary nitrates (0.4 to 0.6 mg) and/or verapamil (0.2 to 0.3 mg) and repeat PTCA. A recovery of flow of ≧1 TIMI grade was eventually obtained in 3 patients.

TABLE 2

Clinical Events

|  | Adenosine (n = 27) | Saline (n = 27) | P |
|---|---|---|---|
| Recurrent angina and/or ischemia | 3(11) | 2(7) | NS |
| Nonfatal AMI | 0(0) | 1(4) | NS |
| Heart failure | 2(7) | 5(18) | NS |
| Cardiac death | 0(0) | 5(18) | 0.02 |
| Cumulative clinical end points | 5(18) | 13(48) | 0.03 |

Data are presented as number (%) of patients. Cumulative clinical endpoint: recurrent angina and/or ischemia, non-fatal AMI, heart failure, cardiac death.

Clinical Course

Patients received standard pharmacological treatment, including anticoagulant and antiplatelet agents, ACE inhibitors, β-blockers, and nitrates, unless contraindicated. Admission time was 9.1+0.8 days in the adenosine group and 10.2±0.6 days in the saline group (P=NS). Peak CK was 1994±1782 U/L in the adenosine group and 2803±1857 U/L in the saline group (P=NS). Peak CK-MB was 156±142 UAL in the adenosine group and 346±169 U/L in the saline group (P=NS). Three patients in the adenosine group and 2 in the saline group had recurrence of angina (Table 2). These patients underwent repeat angiography, which in 2 cases was followed by repeat PTCA for the treatment of early restenosis. One patient in the saline group suffered a nonfatal MI (Table 2). Two patients in the adenosine group had a clinical diagnosis of heart failure, versus 5 in the saline group (Table 2). None of these differences were statistically significant Five patients in the saline group died in hospital. Two deaths were associated with occlusion of the infarct-related artery and fatal MI, 2 with development of intractable cardiogenic shock, and 1 with AMI in a remote area. No deaths occurred in the adenosine group (P<0.02) (Table 2,). Seven of the 8 patients presenting with the no-reflow phenomenon had adverse events.

Sixteen patients in the adenosine group and 23 in the saline group developed a Q-wave ML (P<0.04).

The composite end point of recurrent angina, nonfatal MI, heart failure, and cardiac death was present in 5 patients in the adenosine group and in 13 patients in the saline group (P<0.03) (Table 2,).

Left Ventricular Function

Serial ventricular function data from good-quality echocardiograms were available in 23 patients of the adenosine group and in 20 patients of the saline group. A total of 114 dyssynergic segments were identified in the admission echocardiogram of the patients included in the adenosine group and 109 in the admission echocardiogram of the patients included in the saline group. In the echocardiogram repeated after 1 week, wall motion was found to be improved in 73 (64%) of the initially dyssynergic segments in the adenosine group and in 39 segments (36%) in the saline group (P=0.0001). Worsening of wall motion was observed in 3 segments (2%) in the adenosine group and in 22 segments (29%) in the saline group (P=0.0001) (FIG. 3). Regional wall motion was unchanged in 38 segments in the adenosine group and in 48 segments in the saline group.

What is claimed is:

1. A method of preventing or inhibiting reperfusion injury to a human following angioplasty, comprising:
   a) positioning a balloon catheter proximate to the obstruction of an infarct-related artery and inflating the balloon;
   b) contacting the distal vascular bed with an adenosine receptor agonist; and
   c) deflating the balloon.

2. The method of claim 1, wherein the adenosine receptor agonist is chosen from adenosine, an $A_1$ adenosine receptor agonist or an $A_2$ adenosine receptor agonist.

3. The method of claim 2 wherein the adenosine receptor agonist is adenosine.

4. The method of claim 2, wherein the adenosine receptor agonist is an $A_1$ adenosine receptor agonist or an $A_2$ adenosine receptor agonist.

5. The method of claim 4, wherein the $A_1$ adenosine receptor agonist is chosen from CPA, R-PIA, SDZ WAG 994, AMP-579, and CVT-510.

6. The method of claim 5, wherein the $A_1$ adenosine receptor agonist is CVT-510.

7. The method of claim 4, wherein the $A_2$ adenosine receptor agonist is chosen from WRC-0470, CGS-21680C, AMP-579, UK 14304, MRE-0470, and CVT-3146.

8. The method of claim 7, wherein the $A_2$ adenosine receptor agonist is CVT-3146.

9. The method of claim 3, wherein 4 mg of adenosine is injected into the distal vascular bed over a period of about 30 seconds to about 2 minutes.

10. The method of claim 9, wherein the adenosine is injected into the distal vascular bed over a period of about 1 minute.

* * * * *